(12) United States Patent
Chaniyilparampu et al.

(10) Patent No.: US 8,680,143 B2
(45) Date of Patent: Mar. 25, 2014

(54) ORALLY ACTIVE CURCUMINOID COMPOUNDS

(75) Inventors: Ramchand Nanappan Chaniyilparampu, Chenna (IN); Anitha Krishnan Nair, Chennai (IN); Anuj Kapoor, Chennai (IN); Kiran Bhupathiraju, Andhra Pradesh (IN); Rama Raju Gokaraju, Andhra Pradesh (IN); Ganga Raju Gokaraju, Andhra Pradash (IN); Trimurtulu Golakoti, Andhra Pradesh (IN); Venkateswarlu Somepalli, Andhra Pradesh (IN)

(73) Assignee: Laila Pharmaceuticals Pvt. Ltd., Chennai, IN (US)

( * ) Notice: Subject to any disclaimer, the term of this patent is extended or adjusted under 35 U.S.C. 154(b) by 343 days.

(21) Appl. No.: 13/002,588

(22) PCT Filed: Jul. 6, 2009

(86) PCT No.: PCT/IN2009/000382
§ 371 (c)(1),
(2), (4) Date: Jan. 4, 2011

(87) PCT Pub. No.: WO2010/004579
PCT Pub. Date: Jan. 14, 2010

(65) Prior Publication Data
US 2011/0112190 A1 May 12, 2011

(30) Foreign Application Priority Data
Jul. 7, 2008 (IN) .......................... 1641/CHE/2008

(51) Int. Cl.
*A01N 37/02* (2006.01)
*A01N 37/06* (2006.01)
*A61K 31/225* (2006.01)

(52) U.S. Cl.
USPC ........................................................ 514/548

(58) Field of Classification Search
None
See application file for complete search history.

(56) References Cited

FOREIGN PATENT DOCUMENTS

| WO | 2004/031122 A1 | 4/2004 |
|----|----|----|
| WO | 2006/117077 A1 | 11/2006 |
| WO | 2007/110168 A1 | 10/2007 |
| WO | WO 2008045534 A2 * | 4/2008 |

OTHER PUBLICATIONS

Patani et al., "Bioisosterism: A Rationale Approach to Drug Design," Chem Rev, 1996, vol. 96, No. 8.*

* cited by examiner

*Primary Examiner* — Craig Ricci
*Assistant Examiner* — Jared D Barsky
(74) *Attorney, Agent, or Firm* — Kramer Amado, P.C.

(57) ABSTRACT

The invention discloses a compound of formula (I) wherein, at least one of $R^1$, $R^2$, $R^3$ and $R^4$ is —C(=O)$R_n$, and $R^1$, $R^2 R^3$ and $R^4$ are H or $CH_3$ and $R_n$ is alkyl or alkenyl group. The alkenyl group have one or more number of double bonds either in cis form or trans form or both. In $R_n$, where n is 12 to 30 carbons; and pharmaceutically acceptable salt thereof. The said alkenyl groups are preferably selected from the group consisting of eicosapentaenoic acid (EPA) or DHA (docosahexaenoic acid). This invention further discloses processes for their preparation of compounds of formula I and pharmaceutical compositions that contain these compounds.

(I)

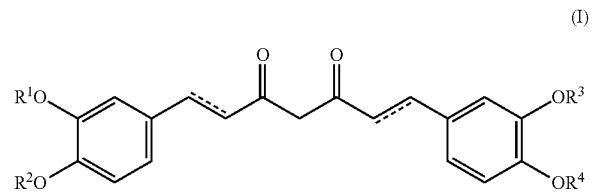

5 Claims, No Drawings

ORALLY ACTIVE CURCUMINOID COMPOUNDS

FIELD OF INVENTION

This invention relates to novel, related and derived compounds of curcumin and its demethylated derivatives (compounds of general formula I), processes for their preparation and pharmaceutical compositions that contain these compounds. The invention further discloses prodrug compounds of curcuminoids

BACKGROUND OF THE INVENTION

A pro-drug is, mostly, pharmacologically inactive compound of active parent drug molecule, which requires enzymatic transformation within the body in order to release the active drug, and that has improved delivery properties over the parent drug. This fact of difference in transport and in-situ effect of characteristics for many drug molecules is the reason for the development of bio-reversible derivatization of drugs, i.e, prodrugs, which is a means by which a substantial improvement in overall efficacy of the parent drugs normally achieved.

In recent years, several types of bio-reversible derivatives have been exploited for proper utilization of drugs. This approach is mainly designed to enhance the solubility of poorly soluble drugs, or to improve the target drug delivery by avoiding hepatic first-pass metabolism or to enhance the stability.

Curcumin and its demethylated derivatives belongs to class of Curcuminoids and are polyphenolic pigments found in the spice turmeric and are responsible for the yellow color of turmeric. Curcuminoids are extracted from *Curcuma longa* belonging to the family Zingiberaccae and commonly known as Turmeric. Curcumin is the active ingredient of the Indian curry spice turmeric and it is one of three curcuminoids of turmeric, along with other two curcuminoids, demethoxycurcumin and bisdemethoxycurcumin. Curcumins are phenolic diarylheptanoids with characteristic yellow colored constituents of turmeric (*Curcuma longa*).

Curcumin acts as a free radical scavenger and antioxidant, inhibiting lipid peroxidation and oxidative DNA damage. Curcumin acts as an inhibitor for cyclo-oxygenase, 5-lipoxygenase and glutathione S-transferase. Curcuminoids induce glutathione S-transferase and are potent inhibitors of cytochrome P450. All the above properties/activities of curcumin is very well documented in the literature.

In recent years, curcumin and its analogs, being natural products, have been the subject of alternative medicine for treatment of various neurodegenerative diseases, particularly, Alzheimers disease. Alzheimer's is a degenerative and terminal disease for which there is no known cure. Alzheimer's disease has been identified as a protein misfolding disease, or proteopathy, due to the accumulation of abnormally folded A-beta and tau proteins in the brains of AD patients.

Despite the beneficial effects of curcumin, the present inventors have noted that there are many bioavailability problems associated with the oral delivery of curcumin. Curcumin does not easily penetrate the human digestive tract and is subject to intestine-based metabolism and rejection, and hence less than 1% of oral curcumin enters the blood plasma. Moreover, the small amount of curcumin that enters the bloodstream is rapidly metabolized by the liver and kidney. Therefore, though curcumin is highly lipophilic (and so easily crosses the blood brain barrier), only very small amounts of orally administered curcumin are registered in the serum and in the brain tissue. Bioavailability studies reveals that ingesting up to 3.6 g of curcumin per day produced a plasma curcumin level in the range of only about 10 nM (Sharma, *Clin. Cancer Res.*, 2004, Oct. 15, 10(20) 6847-54). Another study found that ingesting up to 6-8 g of curcumin per day produced a peak serum level in the range of about 0.51-1.77 µM. Moreover, it has been reported that high oral doses of curcumin in the range of 4,000-8,000 mg/day cause problems such as headache, rash and diarrhea, likely produced by metabolites of curcumin. Therefore, it appears that the above mentioned plasma curcumin concentrations (10 nM-1.77 µM) represent the practical available upper limit of oral dosing of curcumin. Yang, supra, concludes that higher >(5 µM) concentrations of curcumin are not likely to occur in the brain with oral dosing. In fact, Wang reports that injection of 30 mg/kg of curcumin results in a peak curcumin concentration in brain tissue of only about 0.15 ng/mg, which is about 0.40 uM.

It appears that, in the brain tissue concentration range about 1 uM, some but not all of the beneficial therapeutic qualities of curcumin are realized.

Curcumin and its demethylated derivatives have limited bioavailability while administered as oral dosage form due to hepatic first-pass metabolism. In the light of the above bioavailability problems, there exists a need for bioavailable curcumin.

It has been shown that the compounds of formula I fulfill the requirements of active prodrugs; which can effectively be used as oral therapeutic agents at lower doses.

The phrase "bioavailable curcumin" is used to refer the compounds of formula I, of the present invention and hence, wherever, the phrase "bio-available curcumin" appears in the specification, must be construed as a reference to compounds of formula I. Thus, the present invention provides bioavailable curcumin comprising an active constituent of curcumin i.e. bis-O-demethylcurcumin in an effective amount.

SUMMARY OF THE INVENTION

Accordingly, in one aspect, the present invention provides compounds of general formula I

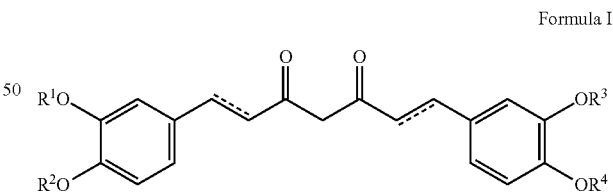

Formula I wherein, at least one of $R^1$, $R^2$, $R^3$ and $R^4$ is $-C(=O)R_n$ and $R^1$, $R^2$, $R^3$ and $R^4$ are H or $CH_3$ and $R_n$ is alkyl or alkenyl group. The alkenyl group has one or more number of double bonds either in cis form or trans form or both. In $R_n$, where n is 12 to 30 carbons;

the  line may be designated as single bond or double bond the alkenyl group ($-C(=O)R_n$) is preferably selected from the following;

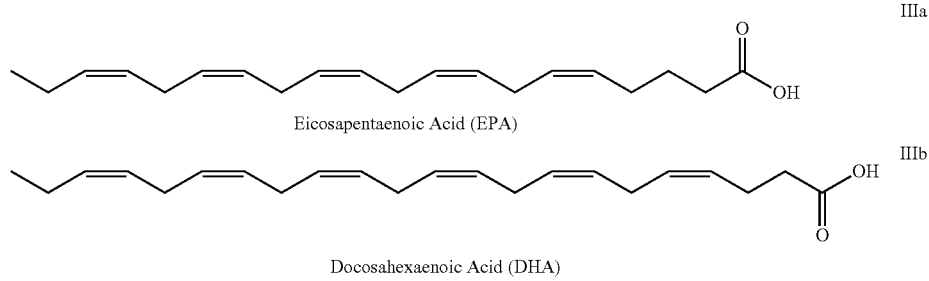

Eicosapentaenoic Acid (EPA)

Docosahexaenoic Acid (DHA)

and pharmaceutically acceptable salts thereof.

It has been found that these compounds can be used as prodrugs of compounds of formula II.

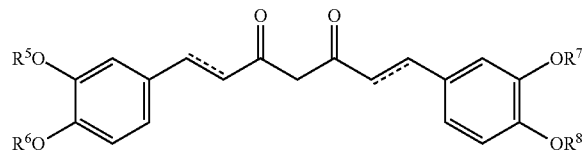

Formula II wherein, $R^5$, $R^6$, $R^7$, $R^8$ are same or different and each individually selected from H or Me the ⇌ line may be designated as single bond or double bond The preferred compounds of formula II are given below. These compounds may be keto or enol forms or in both forms.

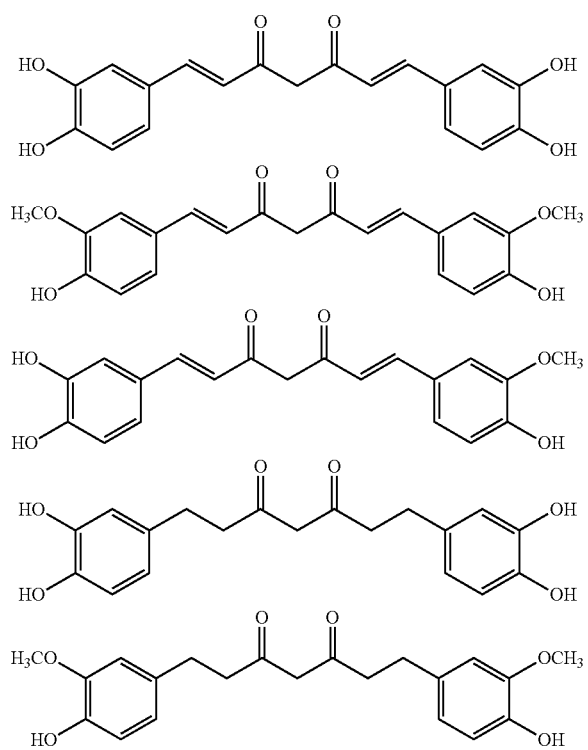

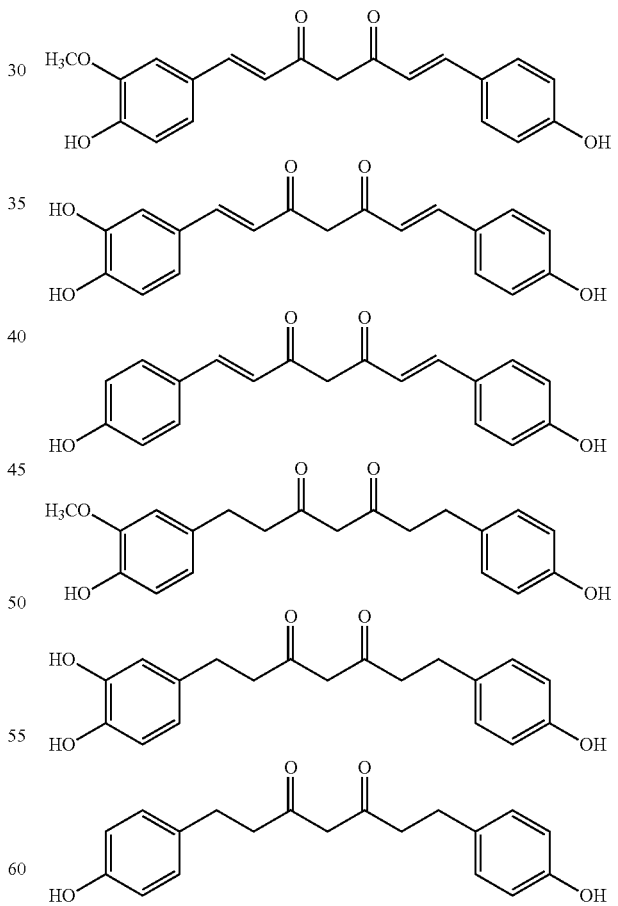

Other preferred precursor compounds for prodrug preparation also includes

In another aspect, the invention provides process for preparation of compounds of formula I, bio available curcumininoid compounds, from compounds of formula II through ester linkages specifically with unsaturated fatty acids such as eicosapentaenoic acid (EPA) or DHA (docosahexaenoic acid) or similar short or long chain saturated or unsaturated fatty acids.

According to the present invention, bio-available oral active compounds of formula I are provided and the predominant compound of formula II referred for the purpose of present invention is bis-O-demethyl curcumin. However, the invention encompasses all the analogous compounds of formula II as mentioned above for the purpose of present invention.

DETAILED DESCRIPTION OF THE INVENTION

The invention will now be described in detail in connection with certain preferred and optional embodiments, so that various aspects thereof may be more fully understood and appreciated.

For the purpose of this invention, the expression "bio available cucumin"; "orally active compounds of formula I"; "orally active prodrugs"; "novel compounds of formula I" are used interchangeably through out the specification and the same may be appreciated as such by the person skilled in the art.

An important aspect about the biochemical composition of the brain is the high amount of lipids and fatty acids. It is well known fact that there exists a blood brain barrier to regulate the transport system of the brain. This barrier does not allow molecules above 500 daltons to enter the brain while small molecules often can enter. Transport of nutrients takes place generally through lipid solubility or specific transporter proteins, similarly a specific transport system exists for fatty acids. Hydrophilic/charged compounds do not have good penetration capacity into the CNS. Therefore, it needs to be more lipophilic in nature in order to be targeted to the brain, as lipophilicity enhances the transport. Therefore, the current inventors have developed an inventive concept of improving the lipophilicity of the compounds of formula II or their analogs, which are particularly useful in treating CNS disorders, through derivatization with fatty acids of varied nature. This derivatization increases lipophilicity of the compounds of formula II and also thereby the transport of molecules into CNS. Thus, the derivatization of compounds of formula II results in orally active prodrugs of formula I, which are particularly useful in CNS related diseases especially once it undergoes hydrolysis.

Combining bis-O-demethylcurcumin or related structures to the carboxylic acid functional group of EPA or DHA through covalent linkages would improve the transport of this prodrug thereby improving its bio-availability and absorption considerably in the brain constituting its therapeutic effects. It is believed that once the pro-drug crosses into the brain, the various non-specific esterases would cleave the bond between the fatty acid and the active drug thus allowing the drug to demonstrate its therapeutic effects especially in the inflamed tissues where transport of fatty acids is high and also the esterase activity.

Thus, when bis-O-demethylcurcumin or related structures are covalently linked to the carboxylic acid functional group of long chain fatty acids like EPA or DHA, it can be easily transported into the brain where it undergoes enzymatic cleavage of the covalent bond between the fatty acid and bis-O-demethylcurcumin/related structures thereby enhancing bis-O-demethylcurcumin/related structures to demonstrate its anti amyloid or anti oxidant effect or anti-inflammatory effect or any other therapeutic effects it may have due to increased bioavailability and significantly improved pharmacokinetic properties.

As discussed earlier, Bis-O-demethylcurcumin does not easily penetrate the human digestive tract and is subject to intestine-based metabolism and rejection, less than 1% of oral bis-O-demethylcurcumin enters the plasma. Secondly, the small amount of curcumin that enters the bloodstream is rapidly metabolized by the liver and kidney. Therefore, although bis-O-demethylcurcumin is highly lipophilic (and so easily crosses the blood brain barrier), only very small amounts of orally administered bis-O-demethylcurcumin are registered in the serum and in the brain tissue, due to the above reasons.

Thus, in order to overcome the above bioavailable problems, novel active compounds of general formula I, i.e. orally active prodrug compounds of formula II or other such compounds are provided by the present invention and these compounds will improve drug bioavailability to the brain, thereby avoiding extensive hepatic first-pass metabolism which significantly lowers the plasma and brain concentrations of compounds of formula II, viz., bis-O-demethylcurcumin when administered orally. Therefore, small doses of the novel orally active prodrugs of bis-O-demethylcurcumin or its analogs can be administered which will result in fewer side effects, and the drug will be more tolerable and more effective. Drugs such as bis-O-demethylcurcumin being lipophilic generally achieve higher brain levels after the administration in pro-drug form than the oral or intravenous administration of the drug as such.

The present invention, therefore, describes novel and therapeutically active compounds of formula I prepared from long chain unsaturated fatty acids and bis-O-demethylcurcumin or related structures, method of preparation, compositions and its use as a therapeutic. In one embodiment, the present invention provides compounds of general formula I, Formula I

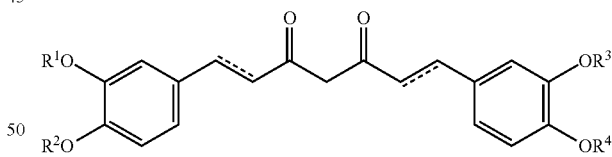

Wherein, at least one of $R^1$, $R^2$, $R^3$ and $R^4$ is —C(=O)$R_n$, and $R^1$, $R^2$, $R^3$ and $R^4$ are H or $CH_3$ and $R_n$ is alkyl or alkenyl group. The alkenyl group have one or more number of double bonds either in cis form or trans form or both. In $R_n$, where n is 12 to 30 carbons;

the ⇢ line may be single bond or double bond
the alkenyl group is preferably selected from the following;

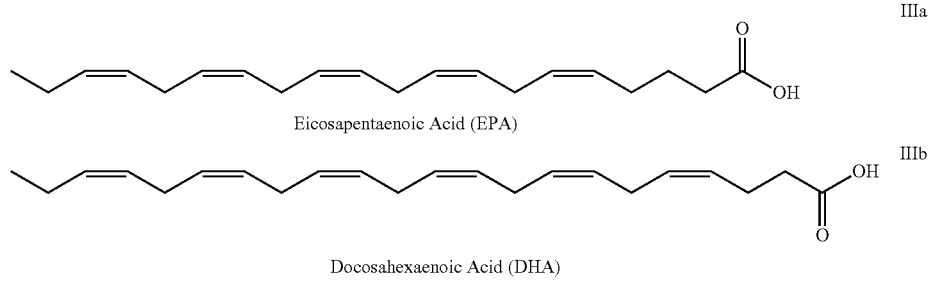

Eicosapentaenoic Acid (EPA)　IIIa

Docosahexaenoic Acid (DHA)　IIIb and pharmaceutically acceptable salts thereof.

It has been found that these compounds can be used as prodrugs of compounds of formula II.

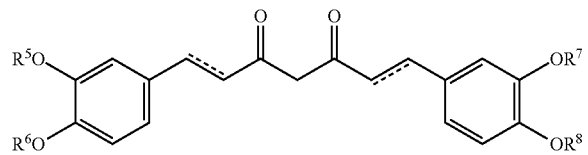

Formula II

Wherein, $R^5$, $R^6$, $R^7$, $R^8$ may be same or different and each individually selected from H or Me the ⤳ line may be designated as single bond or double bond The novel compounds of the formula I of the present invention are preferably made from the compounds of formula II, but other compounds listed below can also be used. These compounds may be keto or enol forms or in both forms.

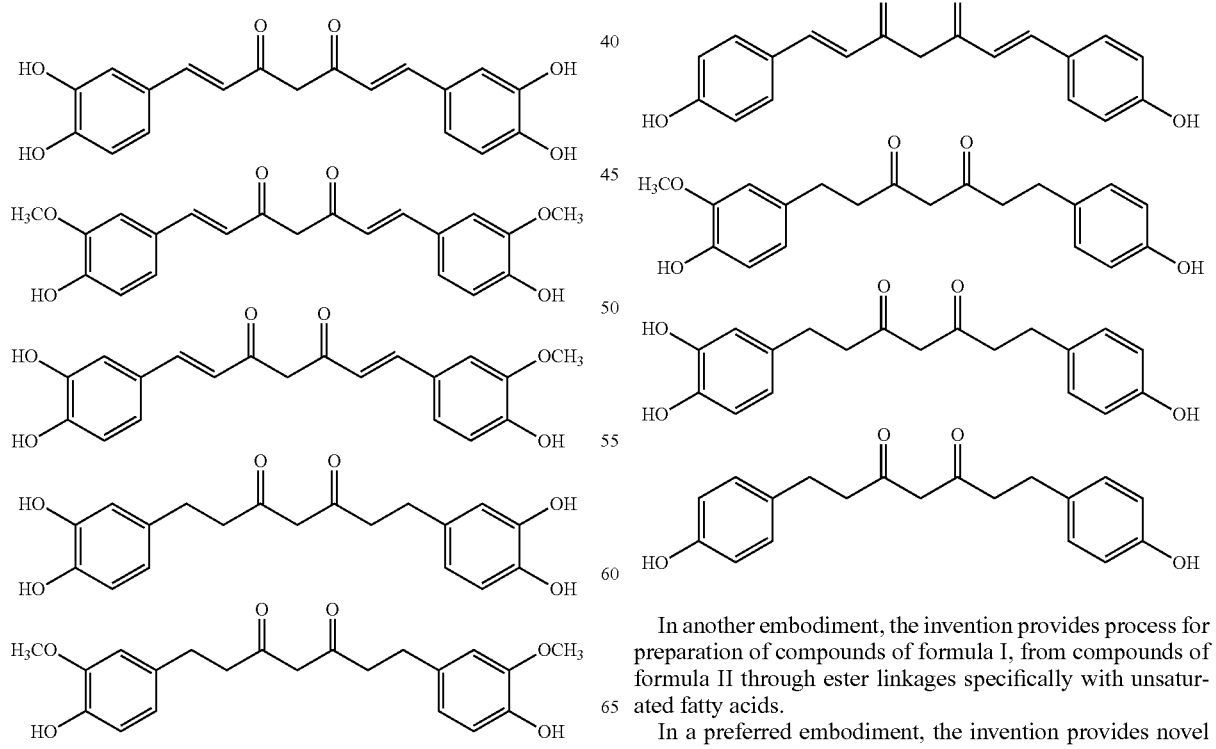

Other preferred precursor compounds for the preparation of novel compounds of formula I also includes In another embodiment, the invention provides process for preparation of compounds of formula I, from compounds of formula II through ester linkages specifically with unsaturated fatty acids.

In a preferred embodiment, the invention provides novel and therapeutically active compounds prepared from compounds of formula II, preferably bis-O-demethylcurcumin or related structure using long chain unsaturated fatty acids. The current invention predominantly deals with pharmacologically active combination of eicosapentaenoic acid (EPA) or DHA (docosahexaenoic acid) or similar short or long chain saturated or unsaturated fatty acids covalently linked to bis-O-demethylcurcumin or related structures showing anti-oxidant and/or anti-inflammatory properties/regulating gene transcription and translation.

According to the present invention, the preferred bio-available oral active compounds of formula I is prepared from compound of formula II, preferably bis-O-demethyl curcumin using EPA or DHA or similar short or long chain saturated or unsaturated fatty acids for the purpose of present invention. The preferred compounds of the orally active pro-drug of bis-O-demethyl curcumin is shown below:

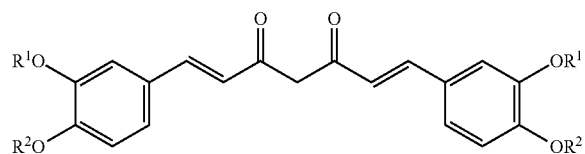

Wherein $R^1$ and $R^2$ may be same or different, each selected from the group consisting of EPA or DHA or similar short or long chin saturated or unsaturated fatty acid moiety. However, the present invention encompasses all the analogous compounds of formula II as mentioned above.

Therefore, the administration of bis-O-demethylcurcumin via orally active prodrug compounds of the invention may deliver the drug on target site and thus helps to enhance the effectiveness of bis-O-demethylcurcumin in the brain (the site of action). Additionally, as bis-O-demethylcurcumin is heavily metabolized by the liver, administration as a pro-drug may help to reduce drug interactions with other drugs that are also extensively metabolized by the liver.

The present invention thus, predominantly relates to pharmacologically active combination of eicosapentaenoic acid (EPA) or DHA (docosahexaenoic acid) or similar short or long chain saturated or unsaturated fatty acids covalently linked to bis-O-demethylcurcumin or to its related/analogous structures showing anti-oxidant and/or anti-inflammatory properties/regulating gene transcription and translation.

The present invention further discloses pharmaceutical compositions comprising the compounds of formula I in association with one or more suitable pharmaceutical excipients selected from fillers, diluents, disintegrants etc.

In accordance with the present invention there is provided a process for preparation of compounds of general formula I, wherein said process comprises the following steps:
a) As a first step the carboxylic acid functionality of the fatty acid needs to be activated for the covalent linking to take place. This activation can be performed by any one of the following methods: 1) using the activation agents like certain carbodiimides in the presence of polar aprotic or protic solvents most preferable being polar aprotic solvents; 2) Formation of active esters such as N hydroxysuccinate ester with the use of carbodiimides and reacting it with pharmaceutically active substance 3) Anhydride formation with chloroformates or with other acid chlorides to give anhydrides of EPA or DHA; 4) Formation of acid chloride of EPA or DHA using thionyl chloride or oxalyl chloride or phosphorous halides in the presence of polar aprotic or combination of non-polar aprotic and polar aprotic solvents like DMSO or DMF preferably in non-polar aprotic solvents like toluene or diisopropyl ether.

The activation process needs to be performed under mild conditions as the double bonds in the long chain PUFA's are susceptible to harsh reaction conditions.

b) The condensation reaction of activated long chain PUFA and bis-βdemethylcurcumin/related structures need to be carried out in appropriate solvents like dichloromethane, tetrahydrofuran, dioxane, DMSO.

Thus, the process for preparation of general compounds of formula I is schematically provided in scheme 1 and scheme 2 below:

Alternatively, the interfering functionalities of bis-O-demethylcurcumin/related structures like OH etc, can be protected by converting them as suitable derivatives thus allowing only the functionality of interest to be involved in the covalent linking with the fatty acids and proceeded through steps (a) and (b) to get the compounds of formula I.

Further, alternatively the compounds of structures of the formula II are treated directly under controlled reaction conditions with pre-calculated number of mole equivalents of long chain PUFA in the presence of an activating agent such as DCC to directly obtain the compounds of formula I.

Scheme 1

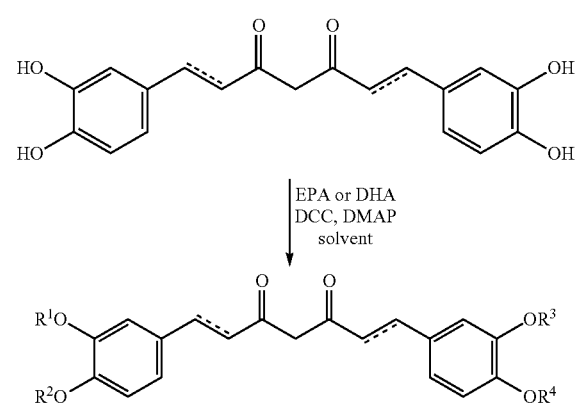

Wherein, at least one of $R^1$, $R^2$, $R^3$ and $R^4$ is —C(=O)$R_n$ and $R^1$, $R^2$, $R^3$ and $R^4$ are H or $CH_3$ and $R_n$ is alkyl or alkenyl group. The alkenyl groups have one or more number of double bonds either in cis form or trans form or both. In $R_n$, where n is 12 to 30 carbons.

The ⇝ line may be designated as single bond or double bond

Alternatively, the compounds of general formula I can be prepared using the method represented in scheme 2 below:

Scheme 2

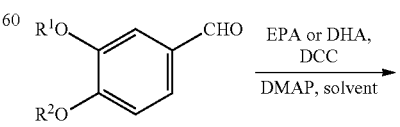

$R^1$ = H and $R^2$ = Alkyl Or
$R^1$ = alkyl and $R^2$ = H

-continued

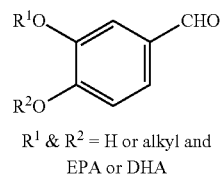

R¹ & R² = H or alkyl and
EPA or DHA

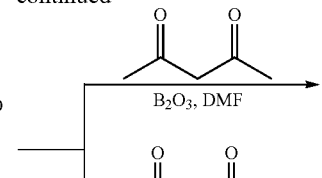

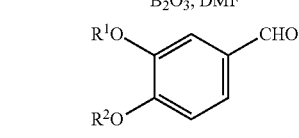

R¹ = H and R² = Alkyl Or
R¹ = alkyl and R² = H

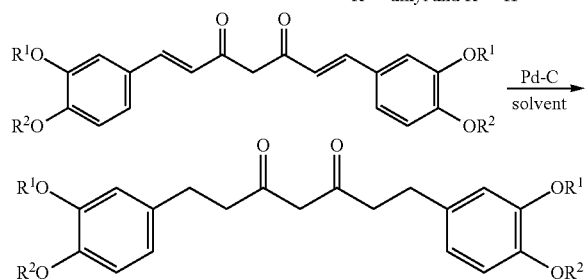

Wherein, at least one of $R^1$, $R^2$, $R^3$ and $R^4$ is —C(=O)$R_n$ and $R^1$, $R^2$, $R^3$ and $R^4$ are H or $CH_3$ and $R_n$ is alkyl or alkenyl group. The alkenyl group have one or more number of double bonds either in cis form or trans form or both. In $R_n$, where n is 12 to 30 carbons; preferably EPA or DHA The process for preparing the prodrug compound of formula I comprises of a) reacting compound of formula IV

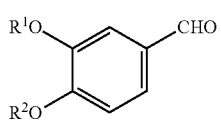

Formula IV wherein, at least one of $R^1$ and $R^2$ my be H and other may be H or $CH_3$, with compound of formula IIIa or IIIb, in the presence of 4-(dimethylamino)pyridine and dicyclohexylcarbodiimide in an organic solvent to form a compound of formula V, wherein at least one of $R^1$ and $R^2$ my be H or $CH_3$ and the other may be selected from formula IIIa or IIIb

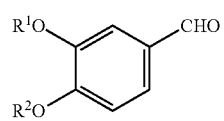

Formula V b) reacting compound of formula V obtained from step 5(a) with acetyl acetone in the presence of boric oxide, trialkyl borate, an organic primary amine or secondary amine in an organic solvent to form compound of formula I.

In the above process, the organic solvent is selected form the group consisting of dimethylformamide, dimethyl sulfoxide, ethyl acetate and dichloromethane.

In the above process, the trialkyl borate is selected from $C_1$ to $C_{10}$ trialkyl borate, preferably tributyl borate and the organic primary amine is preferably n-butylamine and the secondary amine is preferably selected from 1,2,3,4-tertrahydroquinoline The compounds of formula II can be first subjected to reduction using a catalytic reducing agent in a suitable solvent, preferably Pd/carbon in alcohol to reduce the double bonds and the reduced product is then coupled with EPA or DHA to form the compounds of formula I.

Alternatively, the EPA or DHA coupled compounds of formula I are prepared as per the scheme 2 and the coupled product is subjected to reduction using a catalytic reducing agent in a suitable solvent, preferably Pd/carbon in alcohol The method of linking long chain PUFA (poly unsaturated fatty acids) and drugs covalently is widely reported. For eg. Methods of activation of carboxylic acid functionality, protecting interfering functionalities etc are reported in literatures. However, the condensation of long chain PUFA with bis-O demethylcurcumin/related structures, which is a novel concept and has not been reported till now for the purpose of drug delivery to the brain or intestine or inflamed tissue or cancer cells or any other parts of the human body.

Thus the compounds of the invention have two active components in its structure. The basic active ingredient which will interact with receptors, ion channels, transduction and translation protein etc, whereas molecules like EPA, DHA or fatty acids which are covalently linked will change the lipophilicity of whole molecule thereby increasing transport trans-intestinally as well as tissue, inflammed tissues, cancerous tissues or brain. Apart from enhancing the transport after linking; after hydrolyzing into fatty acids, there will be a good synergy between the active drug and the fatty acids, as molecules like EPA, and DHA are known to regulate inflammatory cascades, MAPK pathways etc thus into several therapeutic segments.

Thus the present invention achieves novel related compounds of curcumin with enhanced therapeutic benefits prepared from two pharmacologically active compounds.

The present invention is exemplified by the examples given below, which are provided by the way of illustration only, and should not be considered to limit the scope of the invention. Variation and changes, which are obvious to one skilled in the art, are intended to be within the scope and nature of the invention, which are defined in the appended claims.

EXAMPLES

Example 1

Synthesis of 1-(4-eicosapentaenoyloxy-3-methoxyphenyl)-7-(4-hydroxy-3-methoxy phenyl)-1,6-heptadiene-3,5-dione. [EPA ester of curcumin-1]

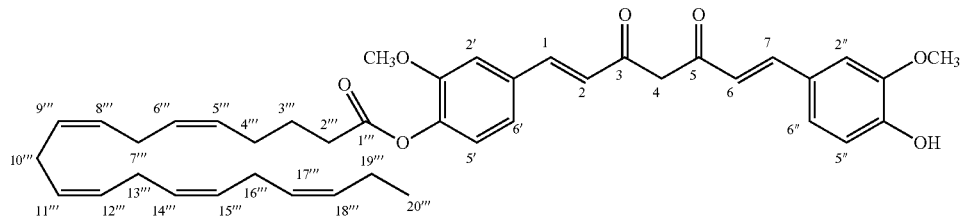

Method A

Cis-eicosapentaenoic acid (EPA)

To a solution of ethyl cis-eicosapentaenoate (5 g, 15.15 mmol) in methanol (100 mL) was added an aqueous solution of sodium hydroxide (6 g, 150 mmol, in 20 mL of water) at rt and stirred for 1.5 h. The reaction mixture was poured into ice cooled water and acidified with dil. HCl. The solution was extracted with dichloromethane (3×50 mL) and the combined layer was washed with water, brine and dried over sodium sulfate. The solution was filtered and evaporated the solvent to give the acid (4.4 g, 96%) as an oil; LCMS (ESI, negative ion mode): m/z 301 (M-H)⁻.

1-(4-Eicosapentaenoyloxy-3-methoxyphenyl)-7-(4-hydroxy-3-methoxy-phenyl)-1,6-heptadiene-3,5-dione To a solution of curcumin (300 mg, 0.81 mmol), cis-eicosapentaenoic acid (250 mg, 0.83 mmol) and catalytic amount of 4-(dimethylamino)pyridine in dichloromethane (10 mL) was added a solution of N,N'-dicyclohexylcarbodiimide (252 mg, 1.2 mmol) in dichloromethane (5 mL) for 5 min at ice cold temperature. The mixture was stirred at rt for 16 h and diluted with water. The dichloromethane layer was separated and the aqueous layer was extracted with dichloromethane (3×100 mL). The combined dichloromethane layer was washed with water, brine and dried over sodium sulfate. The solution was filtered and the residue was chromatographed over silica gel column using hexane-ethyl acetate (90:10) mixture as an eluent to give the product as an oil (235 mg, 44%). IR (neat) $v_{max}$ 3013, 2961, 2929, 1762, 1630, 1593, 1268, 1123, 1032, 970 cm⁻¹; ¹H NMR (CDCl₃) δ 7.61 (1H, d, J=16.0 Hz, H-1), 7.60 (1H, d, J=15.6 Hz, H-7), 7.03-7.16 (5H, m, H-2', 2'', 5', 6', 6''), 6.93 (1H, d, J=8.4 Hz, H-5''), 6.55 (1H, d, J=16 Hz, H-2), 6.49 (1H, d, J=16 Hz, H-6), 5.89 (1H, br s, Ar—OH), 5.83 (1H, s, H-4), 5.38-5.39 (10H, m, H-5''', 6''', 8''', 9''', 11''', 12''', 14''', 15''', 17''', 18'''), 3.95 (3H, s, Ar—OCH₃), 3.87 (3H, s, Ar—OCH₃), 2.84-2.86 (8H, m, H-7''', 10''', 13''', 16'''), 2.58-2.66 (2H, m, H-2'''), 2.22-2.23 (2H, m, H-19'''), 2.05-2.09 (2H, m, H-4'''), 1.82-187 (2H, m, H-3'''), 0.97 (3H, t, J=7.4 Hz, H-20'''); LCMS (ESI, negative ion mode): m/z 651 (M-H)⁻.

Method B

3-Methoxy-4-eicosapentaenoyloxybenzaldehyde

To a solution of vanillin (330 mg, 2.2 mmol), cis-eicosapentaenoic acid (800 mg, 2.65 mmol) and catalytic amount of 4-(dimethylamino)pyridine in dichloromethane (DCM, 15 mL) was added a solution of N,N'-dicyclohexylcarbodiimide (720 mg, 3.53 mmol) in DCM (5 mL) for 5 min at ice cold temperature. The mixture was stirred at rt for 16 h and diluted with water. DCM layer was separated and the aqueous layer was extracted with DCM (3×100 mL). The combined DCM layer was washed with water, brine and dried over sodium sulfate. The solution was filtered and the residue was chromatographed over silica gel column using hexane-ethyl acetate (95:5) as an eluent to give the product as an oil (710 mg, 75%). IR (neat) $v_{max}$ 3012, 2961, 2931, 2855, 1767, 1701, 1600, 1271, 1149, 1119, 1032 cm⁻¹; ¹H NMR (400 MHz, CDCl₃) δ 9.94 (1H, s, —CHO), 7.49 (1H, d, J=1.6 Hz, H-2), 7.47 (1H, dd, J=8.0, 1.6 Hz, H-6), 7.20 (1H, d, J=8.0 Hz, H-5), 5.30-5.48 (10H, m, H-5', 6', 8', 9', 11', 12', 14', 15', 17', 18'), 3.89 (3H, s, —OCH₃), 2.80-2.88 (8H, m, H-7', 10', 13', 16'), 2.58-2.67 (2H, m, H-2'), 2.22-2.25 (2H, m, H-19'), 2.05-2.11 (2H, m, H-4'), 1.81-189 (2H, m, H-3'), 0.97 (3H, t, J=7.4 Hz, H-20').

1-(4-Eicosapentaenoyloxy-3-methoxyphenyl)-7-(4-hydroxy-3-methoxy-phenyl)-1,6-heptadiene-3,5-dione To a solution of boric oxide (183 mg, 2.65 mmol) in DMF (1 mL), was added acetyl acetone (0.236 mL, 2.29 mmol) followed by tributyl borate (1.25 mL, 4.62 mmol) at rt and stirred at 65° C. for 15 min. To the above borate complex, a mixture of 3-methoxy-4-eicosapentaenoyloxybenzaldehyde (1 g, 2.29 mmol) and vanillin (350 mg, 2.29 mmol) was added and stirred for 5 min at the same temperature. A mixture of n-butyl amine (0.045 mL) and acetic acid (0.13 mL) in DMF (1 mL) was added to the reaction mixture and stirred at 90-95° C. for 4 h. After cooling to 15° C., acetic acid (20%, 20 mL) was added with stirring and again the reaction mixture was stirred at 70° C. for another 1 h. Then the mixture was cooled to rt, extracted with chloroform (3×100 mL) and the combined chloroform layer was washed with water, brine and dried over sodium sulfate. The solution was evaporated under vacuum and the residue was chromatographed over silica gel column using hexane-ethyl acetate (85:15) as an eluent to give 1,7-bis(4-eicosapentaenoyloxy-3-methoxyphenyl)-1,6-heptadiene-3,5-dione (100 mg, 10%). Further elution of the column with the same solvent system gave 1-(4-eicosapentaenoyloxy-3-methoxyphenyl)-7-(4-hydroxy-3-methoxyphenyl)-1,6-heptadiene-3,5-dione (350 mg, 24%). LCMS (ESI, negative ion mode): m/z 651 (M-H)

Example 2

Synthesis of 1-(4-docosahexaenoyloxy-3-methoxyphenyl)-7-(4-hydroxy-3-methoxy-phenyl)-1,6-heptadiene-3,5-dione [DHA ester of curcumin-1]

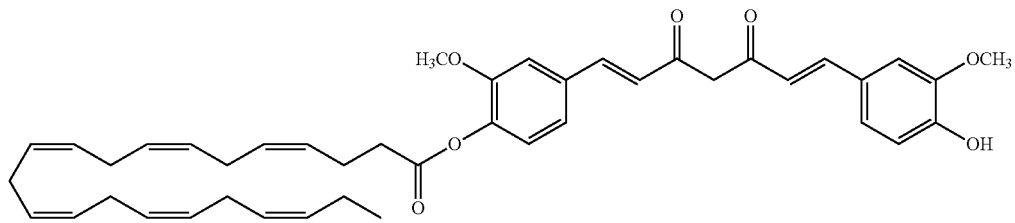 [SMILES: CC/C=C\C/C=C\C/C=C\C/C=C\C/C=C\C/C=C\CCC(=O)Oc1ccc(/C=C/C(=O)CC(=O)/C=C/c2ccc(O)c(OC)c2)cc1OC]

Method A

Cis-docosahexaenoic acid (DHA)

To a solution of ethyl cis-docosahexaenoate (5 g, 14.0 mmol) in methanol (100 mL) was added an aqueous solution of NaOH (6 g, 150 mmol, in 20 mL of water) at rt and stirred for 1.5 h. The reaction mixture was poured into ice cooled water and acidified with dil. HCl. The solution was extracted with DCM (3×50 mL) and the combined layer was washed with water, brine and dried over sodium sulfate. The solution was filtered and the solvent evaporated to give the acid (4.2 g, 91%) as an oil; LCMS (ESI, negative ion mode): m/z 327 (M-H)$^-$.

1-(4-Docosahexaenoyloxy-3-methoxyphenyl)-7-(4-hydroxy-3-methoxy-phenyl)-1,6-heptadiene-3,5-dione To a solution of curcumin (300 mg, 0.81 mmol), cis-docosahexaenoic acid (275 mg, 0.83 mmol) and catalytic amount of 4-(dimethylamino)pyridine in DCM (10 mL) was added a solution of N,N'-dicyclohexylcarbodiimide (252 mg, 1.2 mmol) in DCM (5 mL) for 5 min at ice cold temperature. The mixture was stirred at rt for 16 h and diluted with water. DCM layer was separated and the aqueous layer was extracted with DCM (3×100 mL). The combined DCM layer was washed with water, brine and dried over sodium sulfate. The solution was filtered and the residue was chromatographed over silica gel column using hexane-ethyl acetate mixture (90:10) as an eluent to give the product as oil (250 mg, 45%). IR (neat) $v_{max}$ 3015, 2960, 2930, 1761, 1631, 1593, 1269, 1120, 1031, 972 cm$^{-1}$; $^1$H NMR (CDCl$_3$) δ 7.61 (1H, d, J=16.0 Hz, H-1), 7.60 (1H, d, J=15.6 Hz, H-7), 7.03-7.16 (5H, m, H-2', 2", 5', 6', 6"), 6.93 (1H, d, J=8.4 Hz, H-5"), 6.55 (1H, d, J=16 Hz, H-2), 6.49 (1H, d, J=16 Hz, H-6), 5.89 (1H, br s, Ar—OH), 5.83 (1H, s, H-4), 5.38-5.39 (12H, m, H-4''', 5''', 7''', 8''', 10''', 11''', 13''', 14''', 16''', 17''', 19''', 20'''), 3.95 (3H, s, Ar—OCH$_3$), 3.87 (3H, s, Ar—OCH$_3$), 2.84-2.86 (10H, m, H-6''', 9''', 12''', 15''', 18'''), 2.58-2.66 (2H, m, H-2''), 2.22-2.23 (2H, m, H-21''), 2.05-2.09 (2H, m, H-3'''), 0.97 (3H, t, J=7.4 Hz, H-22'''); LCMS (ESI, negative ion mode): m/z 677 (M-H)$^-$.

Method B

3-Methoxy-4-Docosahexaenoyloxybenzaldehyde

To a solution of vanillin (330 mg, 2.17 mmol), cis-docosahexaenoic acid (870 mg, 2.65 mmol) and catalytic amount of 4-(dimethylamino)pyridine in dichloromethane (15 mL) was added a solution of N,N'-dicyclohexylcarbodiimide (720 mg, 3.50 mmol) in DCM (5 mL) for 5 min at ice cold temperature. The mixture was stirred at rt for 16 h and diluted with water. DCM layer was separated and the aqueous layer was extracted with DCM (3×100 mL). The combined DCM layer was washed with water, brine and dried over sodium sulfate. The solution was filtered and the residue was chromatographed over silica gel column using hexane-ethyl acetate (95:5) mixture as an eluent to give the product as an oil (800 mg, 80%). $^1$H NMR (400 MHz, CDCl$_3$) δ 9.94 (1H, s, —CHO), 7.49 (1H, d, J=1.6 Hz, H-2), 7.47 (1H, dd, J=8.0, 1.6 Hz, H-6), 7.20 (1H, d, J=8.0 Hz, H-5), 5.30-5.48 (12H, m, H-4', 5', 7', 8', 10', 11', 13', 14', 16', 17', 19', 20', 3.89 (3H, s, —OCH$_3$), 2.80-2.88 (10H, m, H-6', 9', 12', 15', 18'), 2.58-2.67 (2H, m, H-2'), 2.22-2.25 (2H, m, H-21'), 2.05-2.11 (2H, m, H-3'), 0.97 (3H, t, J=7.4 Hz, H-22').

1-(4-Docosahexaenoyloxy-3-methoxyphenyl)-7-(4-hydroxy-3-methoxy-phenyl)-1,6-heptadiene-3,5-dione To a solution of boric oxide (183 mg, 2.65 mmol) in DMF (1 mL), was added acetyl acetone (0.236 mL, 2.30 mmol) followed by tributyl borate (1.25 mL, 4.62 mmol) at rt and stirred at 65° C. for 15 min. To the above borate complex, a mixture of 3-methoxy-4-docosahexaenoyloxybenzaldehyde (1 g, 2.30 mmol) and vanillin (350 mg, 2.30 mmol) was added and stirred for 5 min at the same temperature. A mixture of n-butyl amine (0.045 mL) and acetic acid (0.13 mL) in DMF (1 mL) was added to the reaction mixture and stirred at 90-95° C. for 4 h. After cooling to 15° C., acetic acid (20%, 20 mL) was added with stirring and again the reaction mixture was stirred at 70° C. for another 1 h. Then it was cooled to rt, extracted with chloroform (3×100 mL) and the combined chloroform layer was washed with water, brine and dried over sodium sulfate. The solution was filtered and the residue was chromatographed over silica gel column using hexane-ethyl acetate (85:15) as eluents to give 1-(4-docosahexaenoyloxy-3-methoxyphenyl)-7-(4-hydroxy-3-methoxyphenyl)-1,6-heptadiene-3,5-dione (400 mg, 25%). LCMS (ESI, negative ion mode): m/z (M-H)$^-$.

Example 3

Synthesis of a mixture of 1-(4-eicosapentaenoyloxy-3-methoxyphenyl)-7-(4-hydroxy-3-methoxy-phenyl)-1,6-heptadiene-3,5-dione and 1-(4-docosahexaenoyloxy-3-methoxyphenyl)-7-(4-hydroxy-3-methoxy-phenyl)-1,6-heptadiene-3,5-dione [EPA/DHA ester of curcumin-1]

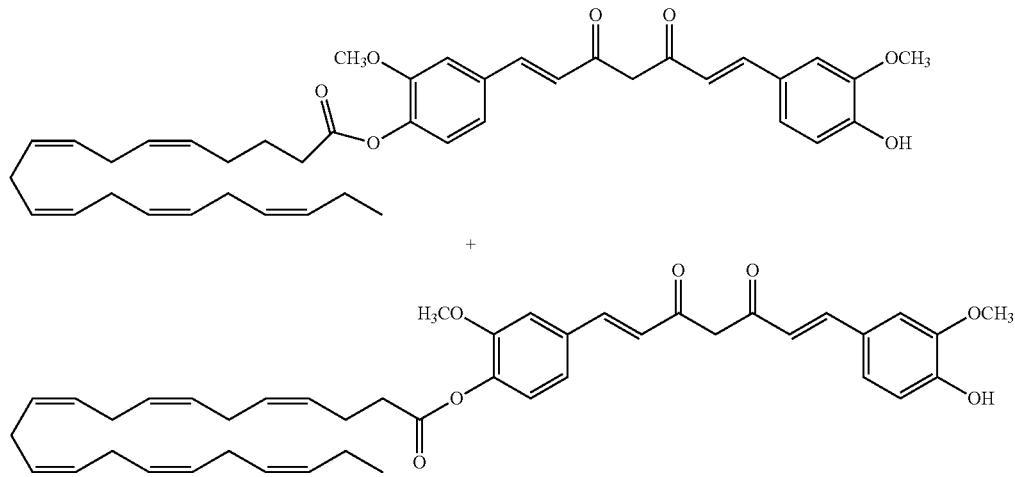

Method A

Mixture of cis-eicosapentaenoic acid and cis-docosahexaenoic acid

To a solution of a mixture of ethyl cis-eicosapentaenoate and ethyl cis-docosahexaenoate (5 g) in methanol (100 mL) was added an aqueous solution of NaOH (6 g, in 20 mL of water) at rt and stirred for 1.5 h. The reaction mixture was poured into ice cooled water and acidified with dil. HCl. The solution was extracted with DCM (3×50 mL) and the combined layer was washed with water, brine and dried over sodium sulfate. The solution was filtered and evaporated the solvent to give the mixture of acids (4.3 g) as an oil; LCMS (ESI, negative ion mode): m/z 301, 327 (M-H)$^-$.

Mixture of 1-(4-eicosapentaenoyloxy-3-methoxyphenyl)-7-(4-hydroxy-3-methoxy-phenyl)-1,6-heptadiene-3,5-dione and 1-(4-docosahexaenoyloxy-3-methoxyphenyl)-7-(4-hydroxy-3-methoxy-phenyl)-1,6-heptadiene-3,5-dione To a solution of curcumin (300 mg), a mixture of cis-eicosapentaenoic acid and cis-docosahexaenoic acid (250 mg) and catalytic amount of 4-(dimethylamino)pyridine in DCM (10 mL) was added along with a solution of N,N'-dicyclohexylcarbodiimide (250 mg) in DCM (5 mL) for 5 min at ice cold temperature. The mixture was stirred at rt for 16 h and diluted with water. DCM layer was separated and the aqueous layer was extracted with DCM (3×100 mL). The combined DCM layer was washed with water, brine and dried over sodium sulfate. The solution was filtered and the residue was chromatographed over silica gel column using hexane-ethyl acetate mixture (90:10) as an eluent to give the product as an oil (250 mg). LCMS (ESI, negative ion mode): m/z 651 and 677 (M-H)$^-$.

Method B

Mixture of 3-methoxy-4-eicosapentaenoyloxybenzaldehyde and 3-methoxy-4-docosahexaenoyloxybenzaldehyde To a solution of vanillin (330 mg), a mixture of cis-eicosapentaenoic acid and cis-docosahexaenoic acid (850 mg) and catalytic amount of 4-(dimethylamino)pyridine in dichloromethane (15 mL) was added along with a solution of N,N'-dicyclohexylcarbodiimide (720 mg) in DCM (5 mL) for 5 min at ice cold temperature. The mixture was stirred at rt for 16 h and diluted with water. DCM layer was separated and the aqueous layer was extracted with DCM (3×100 mL). The combined DCM layer was washed with water, brine and dried over sodium sulfate. The solution was filtered and the residue was chromatographed over silica gel column using hexane-ethyl acetate (95:5) mixture as an eluent to give the product as an oil (800 mg).

Mixture of 1-(4-eicosapentaenoyloxy-3-methoxyphenyl)-7-(4-hydroxy-3-methoxy-phenyl)-1,6-heptadiene-3,5-dione and 1-(4-docosahexaenoyloxy-3-methoxyphenyl)-7-(4-hydroxy-3-methoxy-phenyl)-1, 6-heptadiene-3,5-dione To a solution of boric oxide (183 mg) in DMF (1 mL), was added acetyl acetone (0.236 mL) followed by tributyl borate (1.25 mL) at rt and stirred at 65° C. for 15 min. To the above borate complex, a mixture of 3-methoxy-4-eicosapentaenoyloxybenzaldehyde, 3-methoxy-4-docosahexaenoyloxybenzaldehyde (1 g) and vanillin (350 mg) was added and stirred for 5 min at the same temperature. A mixture of n-butyl amine (0.045 mL) and acetic acid (0.13 mL) in DMF (1 mL) was added to the reaction mixture and stirred at 90-95° C. for 4 h. After cooling to 15° C., acetic acid (20%, 20 mL) was added with stirring and again the reaction mixture was stirred at 70° C. for another 1 h. Then it was cooled to rt, extracted with chloroform (3×100 mL) and the combined chloroform layer was washed with water, brine and dried over sodium sulfate. The solution was filtered and the residue was chromatographed over silica gel column using hexane-ethyl acetate mixture (85:15) as an eluent to give a mixture of 1-(4-eicosapentaenoyloxy-3-methoxyphenyl)-7-(4-hydroxy-3-methoxy-phenyl)-1,6-heptadiene-3,5-dione and 1-(4-docosahexaenoyloxy-3-methoxyphenyl)-7-(4-hydroxy-3-methoxy-phenyl)-1,6-heptadiene-3,5-dione (400 mg). LCMS (ESI, negative ion mode): m/z 651 and 677 (M-H)$^-$.

Example 4

Synthesis of 1,7-bis(4-eicosapentaenoyloxy-3-methoxyphenyl)-1,6-heptadiene-3,5-dione

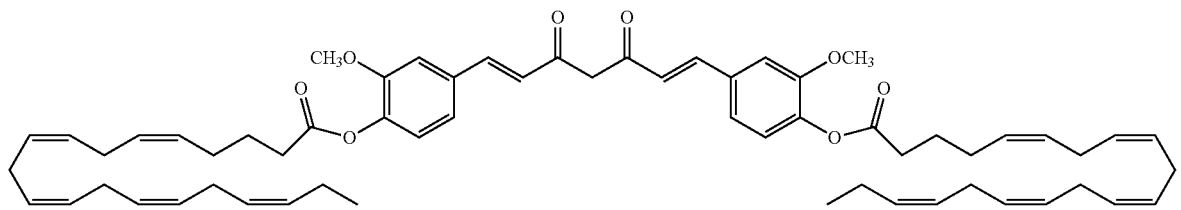

Method A

1,7-Bis(4-eicosapentaenoyloxy-3-methoxyphenyl)-1,6-heptadiene-3,5-dione

To a solution of curcumin (200 mg, 0.54 mmol), cis-eicosapentaenoic acid (380 mg, 1.3 mmol) and catalytic amount of 4-(dimethylamino)pyridine in DCM (15 mL) was added a solution of N,N'-dicyclohexylcarbodiimide (358 mg, 1.73 mmol) in DCM (5 mL) for 5 min at ice cold temperature. The mixture was stirred at rt for 16 h and diluted with water. DCM layer was separated and the aqueous layer was extracted with DCM (3×100 mL). The combined DCM layer was washed with water, brine and dried over sodium sulfate. The solution was filtered and the residue was chromatographed over silica gel column using hexane-ethyl acetate mixture (90:10) as an eluent to give the product as an oil (250 mg, 49%). IR (neat) $v_{max}$ 3011, 2969, 2930, 1763, 1630, 1597, 1299, 1256, 1200, 1123, 1033, 971 cm$^{-1}$; $^1$H NMR (CDCl$_3$) δ 7.62 (2H, d, J=15.6 Hz, H-1, 7), 7.16 (2H, dd, J=8.0, 1.6 Hz, H-6', 6"), 7.12 (2H, d, J=1.6 Hz, H-2', 2"), 7.05 (2H, d, J=8.4 Hz, H-5', 5"), 5.86 (1H, s, H-4), 5.30-5.49 (20H, m, 2×H-5''', 6''', 8''', 9''', 11''', 12''', 14', 15''', 17''', 18'''), 3.87 (6H, s, 2×Ar—OCH$_3$), 2.79-2.88 (16H, m, 2×H-7''', 10''', 13''', 16'''), 2.52-2.67 (4H, m, 2×H-2'''), 2.20-2.25 (4H, m, 2×H-19'''), 2.04-2.11 (4H, m, 2×H-4'''), 1.82-189 (4H, m, 2×H-3'''), 0.97 (6H, t, J=7.6 Hz, 2×H-20''').

Method B

1,7-Bis(4-eicosapentaenoyloxy-3-methoxyphenyl)-1,6-heptadiene-3,5-dione

To a solution of boric oxide (46 mg, 0.66 mmol) in DMF (0.5 mL), was added acetyl acetone (0.06 mL, 0.57 mmol) followed by tributyl borate (0.32 mL, 1.15 mmol) at rt and stirred at 65° C. for 15 min. To the above borate complex, 3-methoxy-4-eicosapentaenoyloxybenzaldehyde (500 mg, 1.15 mmol) was added and stirred for 5 min at the same temperature. A mixture of n-butyl amine (0.01 mL) and acetic acid (0.01 mL) in DMF (0.5 mL) was added to the reaction mixture and stirred at 80-90° C. for 4 h. After cooling to 15° C., acetic acid (20%, 10 mL) was added with stirring and again the reaction mixture was stirred at 70° C. for another 1 h. Then it was cooled to rt, extracted with chloroform (3×100 mL) and the combined chloroform layer was washed with water, brine and dried over sodium sulfate. The solution was filtered and the residue was chromatographed over silica gel column using hexane-ethyl acetate (90:10) as eluents to give the product as an oil (130 mg, 24%). IR (neat) $v_{max}$ 3011, 2969, 2930, 1763, 1630, 1597, 1299, 1256, 1200, 1123, 1033, 971 cm$^{-1}$.

Example 5

Synthesis of a mixture of 1,7-bis(4-eicosapentaenoyloxy-3-methoxyphenyl)-1,6-heptadiene-3,5-dione (A), 1,7-bis(4-docosahexaenoyloxy-3-methoxyphenyl)-1,6-heptadiene-3,5-dione (B) and 1-(4-eicosapentaenoyloxy-3-methoxyphenyl)-7-(4-docosahexaenoyloxy-3-methoxyphenyl)-1,6-heptadiene-3, 5-dione (C)

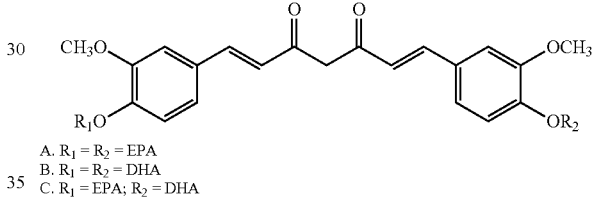

A. $R_1 = R_2 = $ EPA
B. $R_1 = R_2 = $ DHA
C. $R_1 = $ EPA; $R_2 = $ DHA

To a solution of 1,7-bis(3-methoxy-4-hydroxyphenyl)-1,6-heptadiene-3,5-dione (300 mg), a mixture of cis-eicosapentaenoic acid and cis-docosahexaenoic acid (495 mg) and catalytic amount of 4-(dimethylamino)pyridine in methylene dichloride (5 mL) was added along with N,N'-dicyclohexylcarbodiimide (503 mg) in methylene dichloride (3 mL) for 5 min at ice cold temperature. The mixture was stirred at 0-5° C. for 2 h. The mixture was filtered and the solid was washed with methylene dichloride. The filtrate was washed with water and brine, and the solution was dried over sodium sulfate. The solvent was evaporated and the residue was chromatographed over silica gel column using hexane-ethylacetate mixtures. The fraction eluted with 10% ethyl acetate/hexane yielded a mixture of 1,7-bis(4-eicosapentaenoyloxy-3-methoxyphenyl)-1,6-heptadiene-3,5-dione, 1,7-bis(4-docosahexaenoyloxy-3-methoxyphenyl)-1,6-heptadiene-3, 5-dione and 1-(4-eicosapentaenoyloxy-3-methoxyphenyl)-7-(4-docosahexaenoyloxy-3-methoxyphenyl)-1,6-heptadiene-3,5-dione (550 mg) at a ratio of 55.3:11.0:33.7 respectively as an oil. The products were confirmed by a comparison of the mixture with authentic compounds using HPLC method.

Example 6

Synthesis of 1-(4-eicosapentaenoyloxy-3-hydroxyphenyl)-7-(3,4-dihydroxyphenyl)-1,6-heptadiene-3, 5-dione

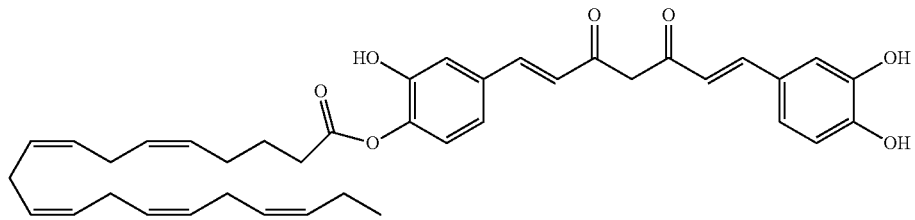 [SMILES: CC/C=C\C/C=C\C/C=C\C/C=C\C/C=C\CCCC(=O)Oc1ccc(/C=C/C(=O)CC(=O)/C=C/c2ccc(O)c(O)c2)cc1O]

To a solution of 1,7-bis(3,4-dihydroxyphenyl)-1,6-heptadiene-3,5-dione (1.0 g, 2.94 mmol), cis-eicosapentaenoic acid (890 mg, 2.94 mmol) and catalytic amount of 4-(dimethylamino)pyridine in tetrahydrofuran (15 mL) was added a solution of N,N'-dicyclohexylcarbodiimide (910 mg, 4.42 mmol) in tetrahydrofuran (5 mL) for 5 min at ice cold temperature. The mixture was stirred at rt for 16 h and diluted with water. The solution was extracted with dichloromethane (3×200 mL) and the combined extract was washed with water, brine and dried over sodium sulfate. The solution was filtered and the residue was chromatographed over silica gel column using hexane-acetone mixture (80:20) as an eluent to give EPA ester of bis-O-demethylcurcumin as an oil (440 mg, 23%). IR (neat) $v_{max}$ 3399, 3013, 2963, 2926, 1736, 1631, 1598, 1298, 1284, 1139, 1124, 965 cm$^{-1}$; $^1$H NMR (DMSO-d$_6$) δ 7.57 (1H, d, J=15.6 Hz, H-1), 7.53 (1H, d, J=15.6 Hz, H-7), 7.45-7.50 (2H, m, H-2", 6"), 7.15 (1H, d, J=2.0 Hz, H-2'), 7.08 (1H, dd, J=8.0, 2.0 Hz, H-6'), 7.01 (1H, d, J=8.0 Hz, H-5"), 6.84 (1H, d, J=8.4 Hz, H-5'), 6.76 (1H, d, J=15.6 Hz, H-2), 6.64 (1H, d, J=15.6 Hz, H-6), 6.10 (1H, s, H-4), 5.37-5.41 (10H, m, H-5''', 6''', 8''', 9''', 11''', 12''', 14''', 15''', 17''', 18'''), 2.80-2.88 (8H, m, H-7''', 10''', 13''', 16'''), 2.60-2.65 (2H, m, H-2'''), 2.21-2.26 (2H, m, H-19'''), 2.04-2.11 (2H, m, H-4'''), 1.75-181 (2H, m, H-3'''), 0.96 (3H, t, J=7.6 Hz, H-20'''); LCMS (ESI, negative ion mode): m/z 623 (M-H)$^-$.

Example 7

Synthesis of 1,7-bis(4-eicosapentaenoyloxy-3-hydroxyphenyl)-1,6-heptadiene-3,5-dione

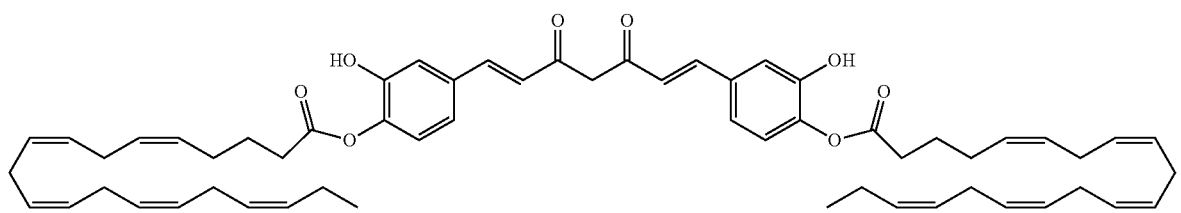

To a solution of 1,7-bis(3,4-dihydroxyphenyl)-1,6-heptadiene-3,5-dione (1.5 g, 4.41 mmol), cis-eicosapentaenoic acid (2.7 g, 8.9 mmol) and catalytic amount of 4-(dimethylamino)pyridine in tetrahydrofuran (20 mL) was added a solution of N,N'-dicyclohexylcarbodiimide (2.72 g, 13.23 mmol) in tetrahydrofuran (5 mL) for 5 min at ice cold temperature. The mixture was stirred at rt for 16 h and diluted with water. The solution was extracted with dichloromethane (3×200 mL) and the combined extracts was washed with water, brine and dried over sodium sulfate. The solution was filtered and the residue was chromatographed over silica gel column using hexane-acetone (85:15) as eluents to give di-EPA ester of bis-O-demethylcurcumin as an oil (1.6 g, 40%). IR (neat) $v_{max}$ 3400, 3012, 2959, 2925, 1746, 1640, 1610, 1241, 1141, 1107, 1021, 971 cm$^{-1}$; LCMS (ESI, negative ion mode): m/z 907 (M-H)$^-$.

Example 8

Synthesis of a mixture of 1,7-bis(4-eicosapentaenoyloxy-3-hydroxyphenyl)-1,6-heptadiene-3,5-dione, 1,7-bis(4-docosahexaenoyloxy-3-hydroxyphenyl)-1,6-heptadiene-3,5-dione and 1-(4-eicosapentaenoyloxy-3-hydroxyphenyl)-7-(4-docosahexaenoyloxy-3-hydroxyphenyl)-1,6-heptadiene-3,5-dione

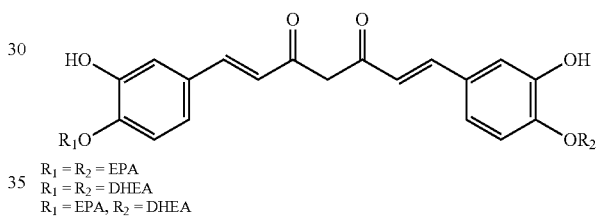

$R_1 = R_2 = EPA$
$R_1 = R_2 = DHEA$
$R_1 = EPA, R_2 = DHEA$

To a solution of 1,7-bis(3,4-dihydroxyphenyl)-1,6-heptadiene-3,5-dione (1.0 g), a mixture of cis-eicosapentaenoic acid and cis-docosahexaenoic acid (2.6 g) and catalytic amount of 4-(dimethylamino)pyridine in tetrahydrofuran (20 mL) was added along with a solution of N,N-dicyclohexylcarbodiimide (2.7 g) in tetrahydrofuran (5 mL) for 5 min at ice cold temperature. The mixture was stirred at rt for 16 h and diluted with water. The solution was extracted with dichloromethane (3×200 mL) and the combined extracts was washed with water, brine and dried over sodium sulfate. The solution was filtered and the residue was chromatographed over silica gel column using hexane-acetone (80:10) as eluents to give the product as an oil (1.5 g). HPLC showed that it is mixture of three major compounds and the products were confirmed by their mass data. LCMS (ESI, negative ion mode): m/z 907, 933, 959 (M-H)$^-$.

We claim:

1. A composition comprising a compound of Formula I, a tautomer thereof, or a pharmaceutically acceptable salt thereof;

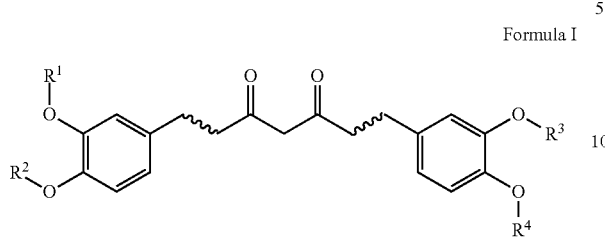

Formula I wherein each of $R^1$, $R^2$, $R^3$ and $R^4$ is selected from the group consisting of H, $CH_3$ and —C(=O)R″; and R″ from —C(=O)R″ is an alkyl or alkenyl group having 12 to 30 carbons, said alkenyl group having one or more double bonds;

wherein at least one of $R^1$, $R^2$, $R^3$ and $R^4$ is —C(=O)R″ and at least three of $R^1$, $R^2$, $R^3$ and $R^4$ are H or —C(=O)R″, and wherein each wavy line ⌇⌇ represents a single bond or a double bond.

2. The composition of claim 1, wherein R″ is an alkenyl group having 12 to 30 carbons, said alkenyl group having at least one cis double bond.

3. The composition of claim 1, wherein R″ is an alkenyl group having 12 to 30 carbons, said alkenyl group having at least one trans double bond.

4. The composition of claim 1, wherein R″ is an alkenyl group having 12 to 30 carbons, said alkenyl group having both a cis double bond and a trans double bond.

5. The composition of claim 1, wherein said composition is a pharmaceutical composition, said pharmaceutical composition further comprising a pharmaceutically acceptable carrier.

* * * * *